United States Patent [19]
Fan et al.

[11] Patent Number: 5,411,891
[45] Date of Patent: May 2, 1995

[54] REAGENT COMPOSITIONS AND THEIR USE IN THE IDENTIFICATION AND CHARACTERIZATION OF RETICULOCYTES IN WHOLE BLOOD

[75] Inventors: Sophie S. Fan, Millwood; Daniel Ben-David, Shrub Oak, both of N.Y.; Gregory M. Colella, Bloomfield, N.J.; Albert Cupo, Scarsdale, N.Y.; Gena Fischer, Harrington Park, N.J.; Leonard Ornstein, White Plains, N.Y.

[73] Assignees: Miles Inc., Tarrytown; Mount Sinai School of Medicine of the City University of New York, New York, both of N.Y.

[21] Appl. No.: 961,582

[22] Filed: Oct. 15, 1992

Related U.S. Application Data

[62] Division of Ser. No. 802,585, Dec. 5, 1991, Pat. No. 5,360,739.

[51] Int. Cl.⁶ ............................................. G01N 33/48
[52] U.S. Cl. ........................................ 436/63; 436/8; 436/10; 436/166; 436/172; 435/2
[58] Field of Search ............... 436/8, 10, 11, 17, 18, 436/63, 172, 800, 520, 521, 522, 546, 166; 435/2

[56] References Cited

U.S. PATENT DOCUMENTS

| | | | |
|---|---|---|---|
| 3,684,377 | 8/1972 | Adams et al. | 356/36 |
| 3,883,247 | 5/1975 | Adams | 356/39 |
| 4,325,706 | 4/1982 | Gershman et al. | 436/63 |
| 4,336,029 | 6/1982 | Natale | 436/172 |
| 4,412,004 | 10/1983 | Ornstein et al. | 436/10 |
| 4,490,353 | 12/1984 | Crawford et al. | 424/52 |
| 4,571,388 | 2/1986 | O'Connel et al. | 436/63 |
| 4,575,490 | 3/1986 | Ornstein et al. | 436/63 |
| 4,707,451 | 11/1987 | Sage, Jr. | 436/63 |
| 4,735,504 | 4/1988 | Tycko | 356/336 |
| 4,745,071 | 5/1988 | Lapicola et al. | 436/18 |
| 4,883,867 | 11/1989 | Lee et al. | 536/28 |
| 4,971,917 | 11/1990 | Kuroda | 436/63 |
| 4,978,624 | 12/1990 | Cremins et al. | 436/17 |
| 4,981,803 | 1/1991 | Kuroda | 436/63 |
| 4,985,174 | 1/1991 | Kuroda et al. | 436/63 |
| 5,039,613 | 8/1991 | Matsuda et al. | 436/63 |
| 5,075,556 | 12/1991 | Fan et al. | 436/63 |
| 5,128,265 | 7/1992 | Meiattini | 436/18 |

FOREIGN PATENT DOCUMENTS

| | | |
|---|---|---|
| 2147999 | 5/1985 | United Kingdom . |
| PCT/WO850-5640 | 12/1985 | WIPO . |

OTHER PUBLICATIONS

Othmer et al. "Encyclopedia of Chemical Technology" 1983 pp. 332, 335.
Jacobberger et al. "Cytometry" 1984 p. 589.
Cytometry, vol. 7 (1986) "Flow Cytometry of DNA Content Using Oxazine 750 or Related Laser Dyes with 633 nm Excitation", Shapiro, et al., pp. 107-110.
Harlow Ed and Lane David, Antibodies, A Laboratory Manual, 1988, p. 103.
Aldrich Catalog of Fine Chemicals, 1988-1989, p. 1097.

Primary Examiner—Donald E. Czaja
Assistant Examiner—Lien Tran
Attorney, Agent, or Firm—Morgan & Finnegan

[57] ABSTRACT

A reagent composition which include an organic cationic dye for staining the reticulocytes in the blood sample and a buffer solution for maintaining a pH of about 6 to about 9 is provided. The dyes may be the red excitable fluorescent dye Oxazine 750, or the blue excitable fluorescent dyes Acridine Orange or derivatives of Acridine Orange. A zwitterionic surfactant is included in the reagent composition for isovolumetric sphering of the reticulocytes and erythrocytes. The reagent composition and whole blood sample mixture is passed through the sensing region of a flow cytometer, the light scattered through at least one angular interval and that fluoresced by each cell is measured, the erythrocytes can be distinguished from reticulocytes and the volume, hemoglobin concentration and the hemoglobin content of each reticulocyte or erythrocyte, and the mean cell volume, mean corpuscular hemoglobin concentration, and mean cell hemoglobin of the reticulocytes and/or erythrocytes are calculated from the measured cell-by-cell volume and hemoglobin concentration.

11 Claims, 12 Drawing Sheets

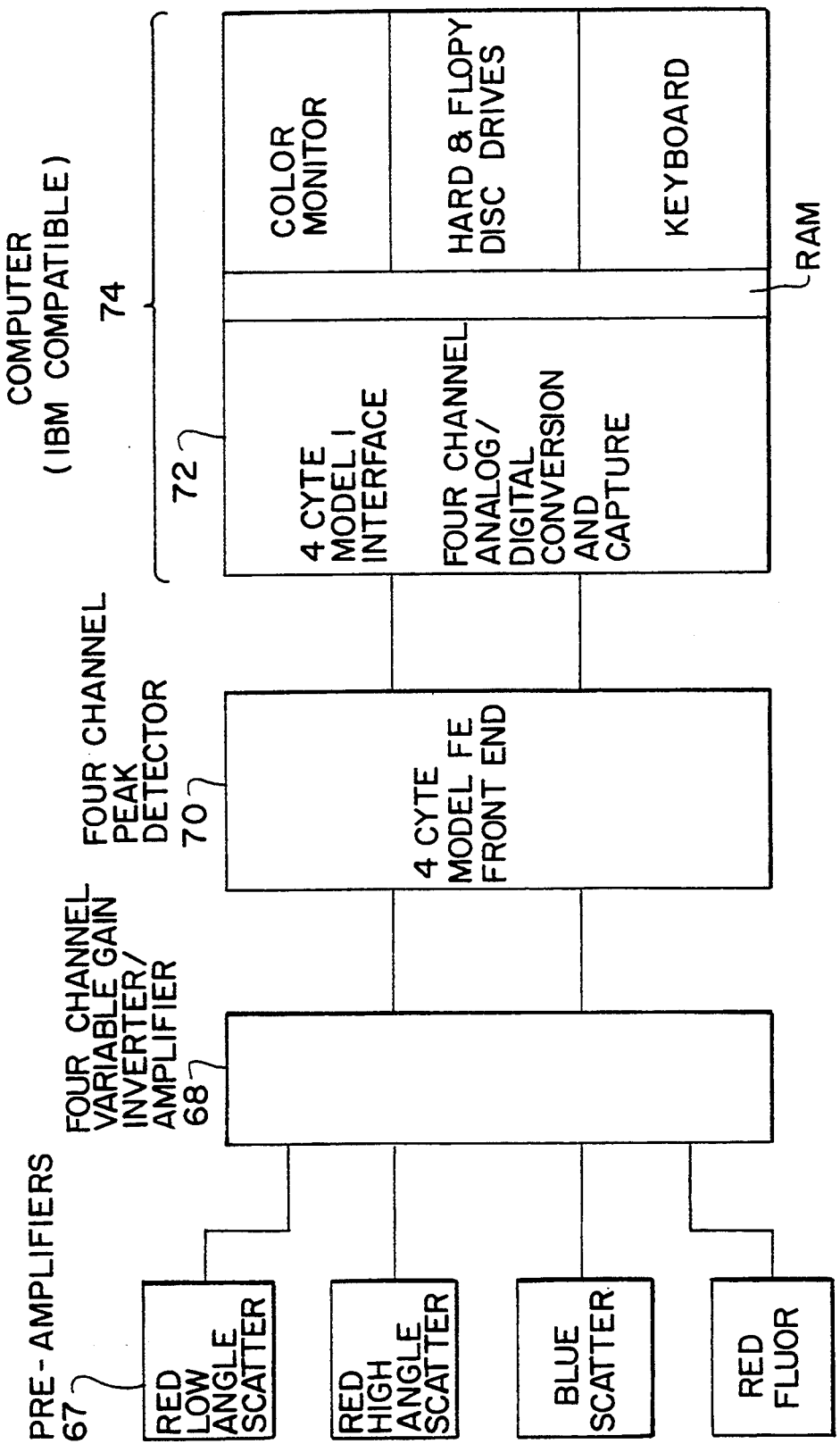
FIG. IC

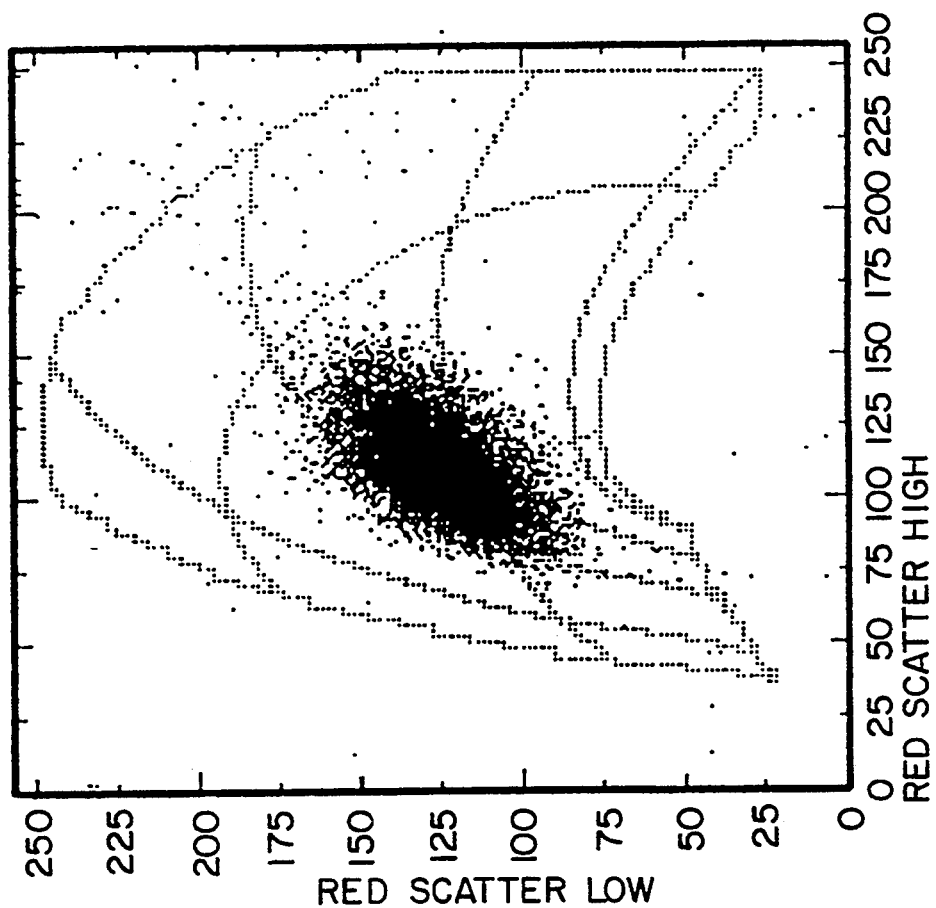
FIG. 2A(2)
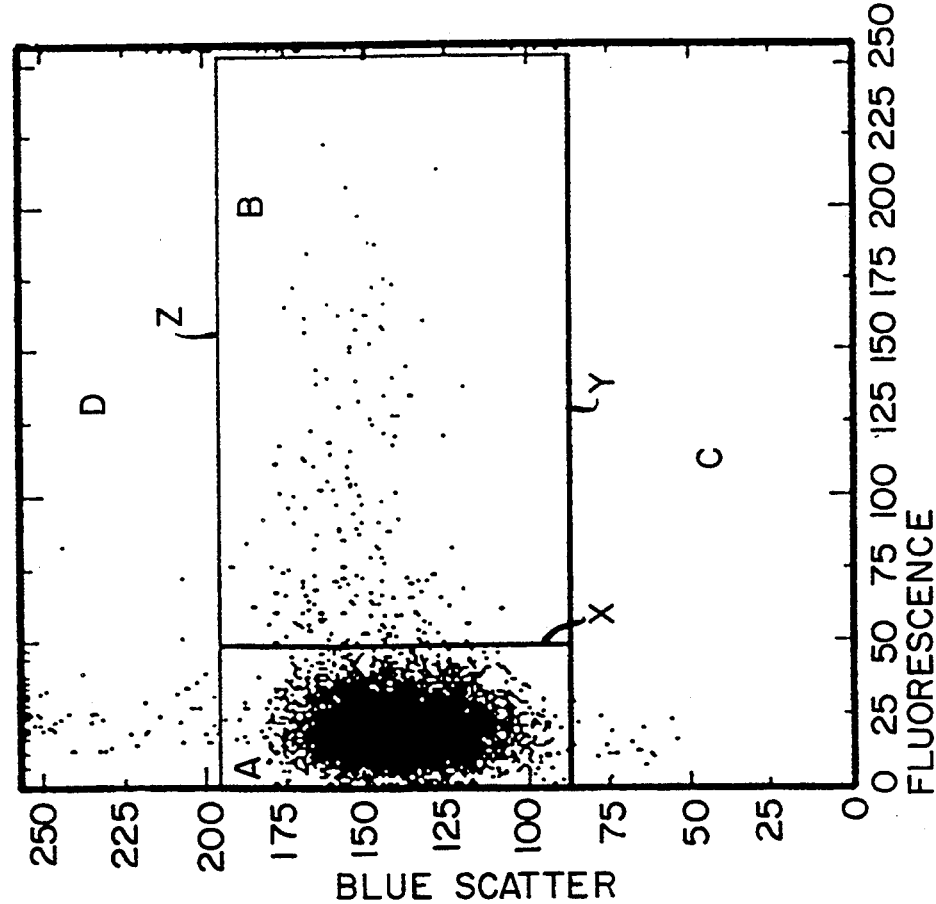
FIG. 2A(1)

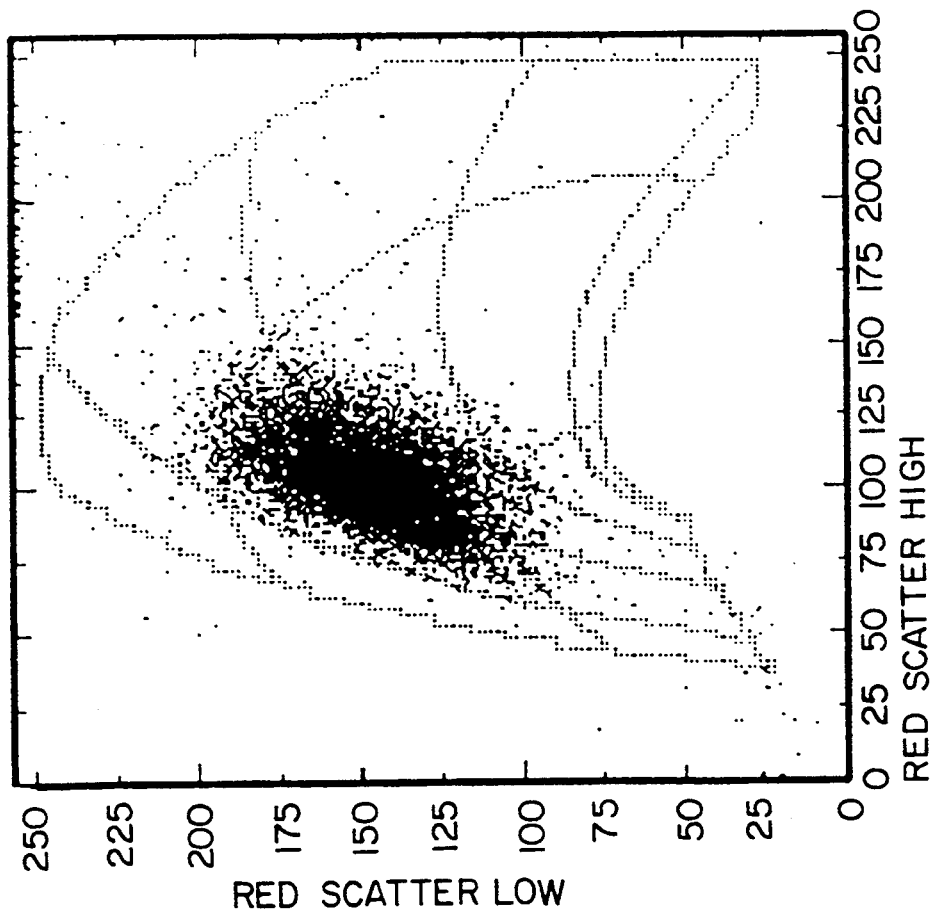
FIG. 2B(1)
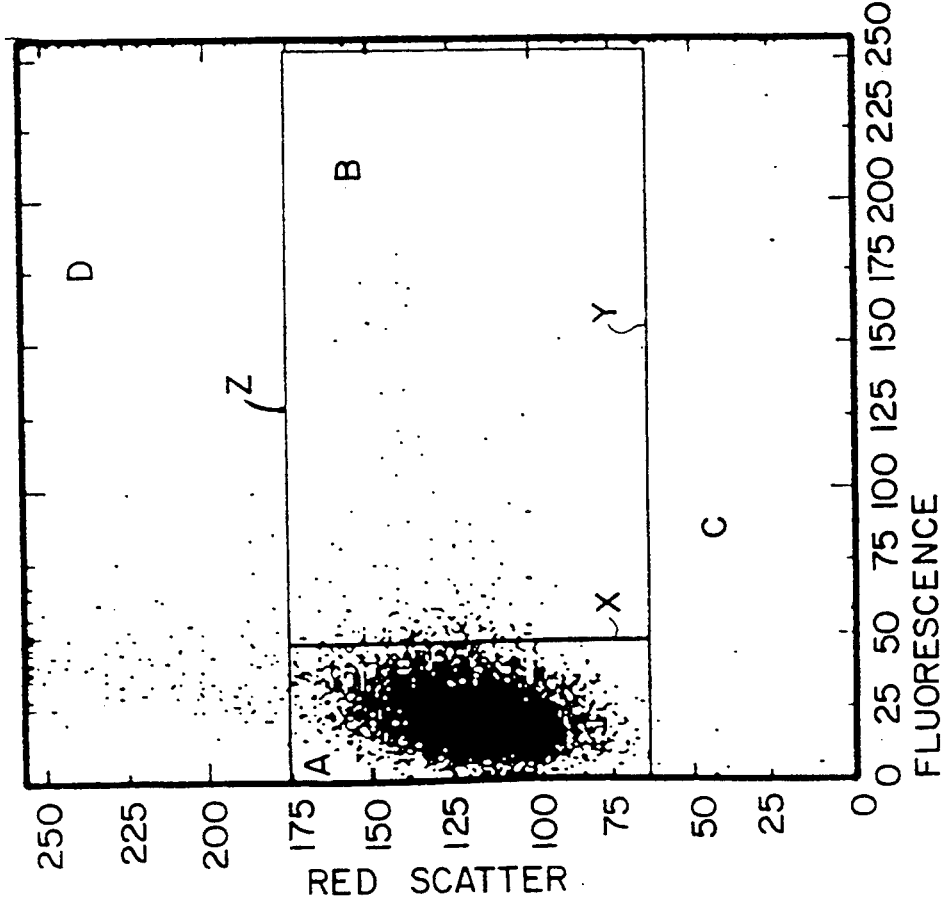
FIG. 2B(2)

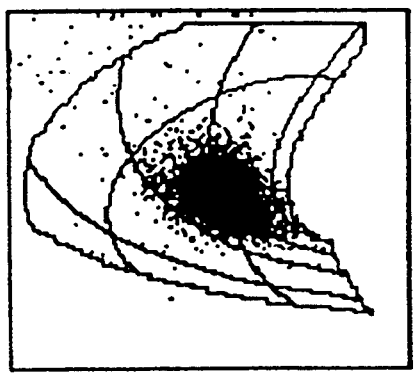 FIG. 6A(2)
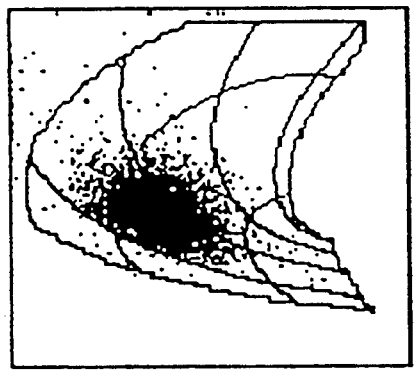 FIG. 6B(2)
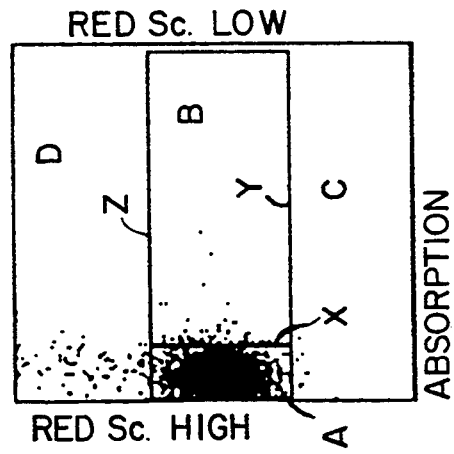 FIG. 6A(1)
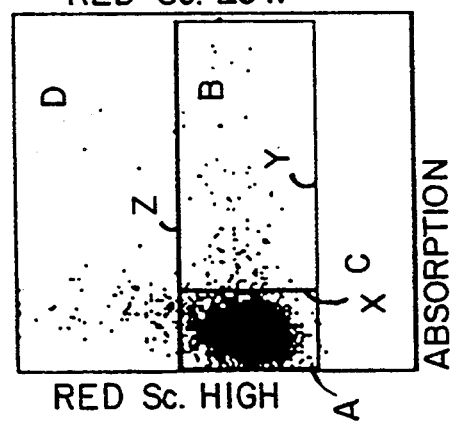 FIG. 6B(1)

REAGENT COMPOSITIONS AND THEIR USE IN THE IDENTIFICATION AND CHARACTERIZATION OF RETICULOCYTES IN WHOLE BLOOD

This is a divisional of application Ser. No. 07/802,585, filed Dec. 5, 1991 now U.S. Pat. No. 5,360,739.

BACKGROUND OF THE INVENTION

1. Field of the Invention

The present invention relates to reagent compositions and their use in identifying and characterizing cells in samples of whole blood, and, more particularly, to reagent compositions and their use in (i) identifying reticulocytes; and (ii) simultaneously measuring the volume, hemoglobin concentration and hemoglobin content of large numbers of individual reticulocytes and erythrocytes, in a whole blood sample by light scatter and flourescence flow cytometry techniques.

2. Description of the Prior Art

In all the higher animals, blood consists of an aqueous fluid part (the plasma) in which are suspended corpuscles of various kinds: the red blood cells (erythrocytes), the white blood cells (leukocytes) and the blood platelets. Plasma has a composition comprising roughly 90% water, 9% protein, 0.9% salts and traces of other materials such as sugar, urea, uric acid and the like.

The cells or corpuscles of the peripheral blood (i.e. the blood outside the bone marrow) are divided into two main groups: erythrocytes, whose primary object is to transport oxygen and leukocytes, whose primary functions relate to the immune system and the destruction of materials foreign to the body. In addition to these two main groups, the blood also contains the so-called blood platelets which are important in hemostasis.

The final stages of erythrocyte maturation occur after their release from the bone marrow while these cells are circulating in the peripheral blood. These young red cells, or "reticulocytes", have lost their nucleus, and thus, their ability to divide or to synthesize ribonucleic acid (RNA). Although these functions have ceased, reticulocytes are still metabolically active and are capable of synthesizing protein, taking up iron for the synthesis of heme, and carrying out the necessary metabolic reactions required to maintain an energy-rich state. These cells are usually most easily distinguished from mature erythrocytes by exposing them to solutions of cationic dyes which react with the anionic RNA in the reticulocytes and precipitate into a fine or coarse stained "reticulum" within the reticulocytes, which gives the reticulocytes their name.

Although reticulocytes normally comprise about 0.5 to 2 percent of the total red blood cell population, this percentage can change dramatically under abnormal conditions. For example, reticulocyte counts have been used for many years as a diagnostic aid in studying blood dyscrasias, as an index of red blood cell regeneration following hemorrhage, as well as for monitoring early toxicity in chemotherapy of certain malignant diseases.

Nucleic acids (RNA and DNA) are polyanions which can be stained with practically any cationic dye. The RNA in reticulocytes can be stained with only a few cationic dyes [including Brilliant Cresyl Blue (BCG), New Methylene Blue (NMB), Auramine O (AuO), Acridine Orange (AO), Thiazole Orange (TO) and Pyronine Y (PY)]. Among these dyes, only a sub-set can be made to penetrate the cells (and therefore stain) rapidly. The sub-set includes NMB and AO. The rate of, and degree of staining of reticulocytes depends upon the extracellular concentration of the dye, the rate of penetration of the dye through the reticulocyte membrane, and the strength of the specific binding constant between the cationic dye and the reticulocyte RNA. The latter two properties are different, and not easily predictable, for each dye, so that trial and error are necessary to discover useful reticulocyte stains. Not all cationic substances are capable of penetrating intact red cells (and reticulocyte) membranes, and the nature of the anions which necessarily accompany the cations, can affect whether or not the cationic substance penetrates rapidly, slowly or not at all. Hydrophobic molecules generally penetrate red cell membranes faster than hydrophilic molecules, and small molecules generally penetrate membranes faster than large molecules. Only a sub-set of salts or buffers mixed with those cationic dyes which can stain reticulocytes permit rapid staining; that is the "right" dye with the "wrong" buffer can take "forever" to stain reticulocytes. Again, trial and error are necessary to discover useful formulations of reticulocyte staining mixtures. Thus, despite various "rules" which can be used as guides, it is not yet possible to predict, a priori, whether, and under which conditions any particular cationic dye may rapidly penetrate and stain reticulocytes.

The fundamental concept of flow cytometry is essentially the passing of cells, one at a time, through a specific sensing region. Typically, by means of hydrodynamic focusing, single cells are passed through the sensing zone, which consists of a focused light source and a detection system for the measurement of scattered, absorbed or fluorescent light. The effect a particle has on the light it intercepts can be detected in a number of ways. In general, the particle has a refractive index which is different than that of the medium in which it is suspended. It will therefore scatter light with which it is illuminated through a range of angles, and with varying intensities, that depend upon that refractive index difference, the particle's size, its shape and any internal variations in refractive index and structure as well as upon the wavelength of the illuminating light. (For homogeneous spheres, Mie Scattering Theory provides a complete description of the distribution and intensities of scattered light.) A particle may also absorb some of the incident light. In the latter case, a portion of the absorbed light may be reemitted as fluorescence, typically at a longer wavelength than the wavelength of the absorbed light.

These and other effects can be measured with light detectors arranged to measure different angular-intervals of scattered light, of unscattered light and of fluorescent light.

When particles are as small as cells, typically less than 15 micrometers in diameter, the numbers of photons in the illuminating beam affected by their passage at high speed (typically hundreds to thousands of widely-spaced cells per second), and especially compared to the number of photons per second falling on the illuminated part of the suspension stream, [and compared to the background illumination of an absorption detector (and even a fluorescence detector)] can be very small. Therefore, the limits of sensitivity of detection of small particular differences between particles depends critically on the photon flux (which depends at least on the intrinsic "brightness" of the light source) and how large the perturbations of the photon flux are that are produced by other small and large differences between particles.

The main sources of interfering noise in absorption, scatter and fluorescence flow cytometry signals can be quite different for each kind of signal. To a first order approximation, the magnitudes of fluorescence signals from stained or unstained cells are almost uninfluenced by shape or orientation of the cells from which the signals arise, whereas scatter and absorption signals are very strongly influenced by shape and orientation. As an extreme example, the native biconcave shape of human erythrocytes has a profound effect on the absorption and scatter signals they generate; effects larger than the small absorption signals of typical classically stained reticulocytes. This is the main reason why, prior to the present co-pending invention described in U.S. application Ser. No. 07/802,593, filed Dec. 5, 1991, now U.S. Pat. No. 5,350,695 entitled "Reagent Compositions and Their Use in the Identification and Characterization of Reticulocytes in Whole Blood" filed concurrently herewith and assigned to the assignees of the present invention, absorption flow cytometry methods have not been useful for reticulocyte counting or generally for the measurement of low concentrations of absorbing molecules in cells. On the other hand, weakly fluorescence materials in cells or (for example, unbound fluorescent dyes) in their surrounding medium has virtually no effect on absorption or scatter signals.

But in fluorescence flow cytometry, when the light source is sufficiently intense, and stray light and system fluorescence have been minimized, the limit of sensitivity for the discrimination of selectively stained cells from unstained cells is set by the relative magnitude of the apparent "background fluorescence" from the components within the unstained cell and/or the level of fluorescence of the medium in the sample stream surrounding the stained and unstained cells. With reticulocyte stains, there is always some equilibrium concentration of dye in solution in the sample stream surrounding the cells. For a given level of binding to reticulum RNA, the ratio of external dye to reticulum-bound dye decreases as the specific binding constant of the dye to RNA increases. Therefore, the higher the binding constant, the lower the necessary external dye concentration, the lower the "background" signal and the higher the signal to noise. Also, if the fluorescence efficiency of the unbound dye is lower than the fluorescence efficiency of the reticulum-bound dye, improved signal to noise is achieved. In fact, the methods which utilize AuO, TO and Thioflavine T, depend upon differences in bound and unbound fluorescence efficiency. The preferred methods described hereinafter, however, depend mainly on high specific binding constants for the high signal to noise achieved, and in one case, the lower non-specific fluorescence of unstained cells at long (red) wavelengths.

Several semi-automated methods are available which can be used for counting the percentage of reticulocytes in an anticoagulated sample of whole blood. In each of the existing methods, a diluent containing an organic cationic dye, such as AO, AuO or TO, is used to stain the RNA within the reticulocytes. The dye penetrates the cell membrane and binds to the RNA and usually precipitates a "reticulum" within each reticulocyte. The amount of the signal from stained RNA is roughly proportional to the RNA content. After proper staining, a fluorescence flow cytometer, equipped with the proper excitation light source (typically an argon ion laser emitting at 488 nm), and emission detection system, can be used to determine the percentage of reticulocytes in the effluent.

Illustrative methods for differentiating reticulocytes in whole blood samples using fluorescent dyes and flow cytometric methods are disclosed in the patent literature.

For example, U.S. Pat. No. 3,684,377 to Adams and Kamentsky discloses a dye composition for differential blood analysis including an aqueous solution of AO, and having a pH factor and osmolality within normal physiological ranges for human blood. The dye composition can be used for counting reticulocytes by measuring the presence or absence of a fluorescence signal with an erythrocyte scatter signal.

U.S. Pat. No. 3,883,247 to Adams discloses a similar method to that of Adams and Kamentsky using a dye composition including AO having a concentration of between $10^{-6}$ and $10^{-5}$ grams per ml.

U.S. Pat. No. 4,336,029 to Natale discloses a reagent composition comprising an aqueous solution of the dye AO, citrate ion and paraformaldehyde at a pH of about 7.4 and an isotonic osmolality. The concentrations of the various ingredients were selected to maximize dye uptake of the reticulocytes and platelets, and provided for dye uptake to be achieved within 2 –5 minutes of mixing the blood sample and reagent composition. An automated method for detection of platelets and reticulocytes utilizing the Natale reagent is disclosed in U.S. Pat. No. 4,325,706 to Gershman, et al.

In the reagent disclosed in U.S. Pat. No. 4,707,451 to Sage, Jr., reticulocytes are stained with thioflavin T or chrysaniline. A whole blood sample was found to be effectively stained by mixing a 25 $\mu$l aliquot of the dye in an isotonic saline solution (0.2 mg/ml) with 10 $\mu$l of anticoagulated whole blood with the mixture incubated for about 7 minutes.

U.S. Pat. No. 4,883,867 to Lee, et al. discloses a dye composition for staining RNA or DNA. The staining composition includes TO as the preferred dye compound. The reticulocytes are stained in a minimum time of 30 minutes.

A reagent for reticulocyte counting of flow cytometric techniques is described in U.S. Pat. No. 4,971,917 to Kuroda which contains a carbonate salt to reduce the non-specific staining of the mature erythrocytes by the dye, e.g., AuO, to prevent the mature erythrocytes from being erroneously counted as reticulocytes when analyzed by fluorescence flow cytometry.

U.S. Pat. No. 4,981,803 describes a reagent for reticulocyte counting which comprises two solutions, namely a stock solution for staining in which a dye AuO is dissolved in a non-aqueous solvent and a buffer solution which satisfies the optimum staining conditions.

Another reticulocyte staining reagent for fluorescence flow cytometric techniques including AuO is disclosed in U.S. Pat. No. 4,985,176 to Kuroda, et al. This reference teaches an incubation time of the reagent and sample of anywhere between 30 seconds and 20 minutes.

As noted above, only a small sub-set of cationic dyes selectively stain reticulocytes, and only a smaller sub-set of these penetrate reticulocytes rapidly. The cationic dye compounds of the present invention stain the reticulocytes in less than 5 minutes so that reticulocyte analysis by flow cytometry can be performed shortly after the blood sample and the reagent composition are mixed together, thus making the present invention readily adaptable for automated procedures.

Quaternized AO derivatives for quantitating reticulocytes are described in copending U.S. patent application Ser. No. 07/444,255, filed Dec. 1, 1989 by Fan and Fischer entitled "Compounds and Reagent Compositions and Their Use in the Quantitative Determination of Reticulocytes in Whole Blood", which is incorporated herein by reference. The Fan, et al. reagent contains $10^{-6}$ gram per ml of an AO derivative in a buffer solution including paraformaldehyde and potassium oxalate. This reagent composition stains reticulocytes to enable the quantitative fluorescence flow cytometric analysis of reticulocytes in a blood sample. Neither this reagent nor any of the above-mentioned reagents contain a sphering agent to prevent orientational noise problems as discussed below, and neither permit simultaneous determination of other diagnostically significant parameters such as volume and hemoglobin concentration of the reticulocytes and erythrocytes on a cell-by-cell basis.

Shapiro and Stevens disclose the use of Oxazine 750 for the determination of DNA content by flow cytometry in *Flow Cytometry of DNA Content Using Oxazine 750 or Related Laser Dyes With 633 nm Excitation*, Cytometry, Vol. 7, pp. 107-110 (1986). The cells are stained by 10 $\mu$M to 30 $\mu$M of Oxazine 750, and are fixed by the addition of ethanol for the DNA determination. Shapiro and Stevens claim that Oxazine 750 does not appear to stain RNA within the cells. Moreover, such protocols with Oxazine 750 do not permit reticulocyte counting or simultaneous determination of other diagnostically significant red blood cell parameters such as volume and hemoglobin concentration on a cell-by-cell basis.

As mentioned above, human and many other mammalian red blood cells have the shape of biconcave disks. The amount of light scattered by such asymmetric red blood cells varies with the orientation of the cell. Accordingly, two identical red blood cells will generate very different scattered light signals as they pass through the sensing zone unless their orientations in the zone are identical. Two red blood cells which are identical, except for the presence in one of a small amount of stained reticulum, generally produce large signal differences on scattered light detectors because of their different orientations.

U.S. Pat. Nos. 4,575,490 and 4,412,004 to Kim and Ornstein teach a method for the elimination of orientational noise in the measurement of the volume of red blood cells in a flow cytometer. Their method involves isovolumetric sphering of unstained red blood cells to eliminate any orientational differences between the cells to permit more precise and accurate measurement of cell volume. Each red blood cell is converted from a biconcave shape to a perfect sphere by a surfactant sphering agent. A "buffering" protein and/or an aldehyde fixing agent are used with the sphering agent to prevent lysis of the erythrocytes. The anionic surfactants described by Kim and Ornstein cannot be used with reticulocyte stains because they have been found to react rapidly with and precipitate the cationic dyes used to stain and precipitate the reticulum.

U.S. Pat. No. 4,735,504 to Tycko discloses the red blood cell channel of the TECHNICON H.1 system, a flow cytometer which provides a fully automated method and means for determining the individual and mean erythrocyte volumes (MCV), and individual and mean corpuscular hemoglobin concentrations (MCHC) of the erythrocytes in an anticoagulated whole blood sample. In this method, the red blood cells in a two microliter aliquot of a whole blood sample are first diluted, and then isovolumetrically sphered using the Kim and Ornstein method just described. After a twenty second incubation period, these cells are passed, essentially one at a time, through the illuminated measurement zone within the red cell channel of the analyzer. The magnitude of the light scattered by these cells into two separate angular intervals is measured. The choice of light source and detection angles are critical in this application. When the light source is a helium neon laser, which emits light at 633 nm, the two scattered light collection angle intervals are two to three degrees (2°–3°) and five to fifteen (5°–15°) degrees. Once the level of the scattered light in each interval is known for a cell, the volume and hemoglobin concentration for that cell are determined by comparison with values predicted by Mie scattering theory. The volume (V) and hemoglobin concentration (HC) for each cell are stored in memory, and the MCV and MCHC are calculated at the completion of the sample measurement cycle by techniques known in the art as discussed in Tycko. The V and HC distribution cytogram and the V and HC histograms are produced using these calculations.

Neither of the above methods distinguishes between reticulocytes and non-reticulocytes, and the methods as previously described and practiced cannot be used to determine separately, the diagnostically significant parameters of the reticulocytes and erythrocytes such as volume and hemoglobin concentration on a cell-by-cell basis.

Another difficulty in monitoring reticulocyte counts with a flow cytometer is difficulty in differentiating between reticulocyte detection signals, mature red blood cell signals, and system noise. The stained strands of RNA are numerous in young reticulocytes, and generate signals of relative large magnitude when detected by a flow cytometer. However, more mature cells contain less stained RNA, and generate smaller signals which may be masked by the noise of the flow cytometer measuring system.

There exists a need for methods and reagents useful for identifying reticulocytes and simultaneously measuring separately the volume, hemoglobin concentration and hemoglobin content of reticulocytes and erythrocytes in a whole blood sample by light scatter and absorption or fluorescence flow cytometry techniques.

We started with the premise that we wanted to use a cationic dye in a variant of well-known art to stain the reticulum. We were also interested in developing flow cytometric methods which could utilize fluorescence to detect reticulocytes. We also hoped, by using isovolumetric sphering and the aforenoted methods of Tycko, that for a fluorescence method, we would be able to simultaneously measure reticulocyte and mature red cell volume and hemoglobin on a cell-by-cell basis using a reagent which also selectively stained reticulocytes. (Note, if the sphering is complete, not isovolumetric, but some known factor X of isotonicity, using Tycko's method with a correction by 1/X for volume and a correction by X for protein, e.g. hemoglobin, concentration, original values can be calculated.)

To utilize Tycko's method, a light source which emits monochromatic light in a region where hemoglobin is very transparent is required; typically a light source like a red helium neon (HeNe) laser, or a laser with even longer wavelength. This means that if that wavelength is also to be used for the absorption measurement, the dye must be a blue dye with a strong absorption of red light.

If the same dye is to be used for fluorescence, it must have a reasonably high quantum efficiency and Stoke's shift, as well as a high binding constant, so that it can be used at a low enough concentration so that stream fluorescence will not unacceptably degrade fluorescence signal to noise ratio. It was discovered that Oxazine 750 not only satisfied the requirements for an absorption/scatter method, but also for a fluorescence/scatter method for determining reticulocyte RNA concentration, cell count and mature and reticulocyte cell volume and hemoglobin content on a cell-by-cell basis. In contrast, NMB, which has a very low fluorescence efficiency, fails for such a fluorescence/scatter method.

Alternatively, at added cost and complexity, using a dye to stain reticulocytes, which fluoresces green to red when excited with blue light, such as AO, AOEOH, TO, AuO, by adding an argon ion or HeCd laser with a 488 nm or 441 nm emission line, and used to illuminate the flow cell coaxially with the red laser, a method is implemented which also permits simultaneous determination of reticulocyte RNA concentration, cell count and mature and reticulocyte cell volume and hemoglobin content on a cell-by-cell basis.

We explored non-ionic, cationic and zwitterionic surfactants for compatibility with cationic dyes, and as red cell sphering agents as would be suggested by the teaching of Kim and Ornstein. As in the Kim and Ornstein method, we used a protein (typically bovine serum albumin) to "buffer" the concentration of the surfactants to slow down red cell lysis. A number of such surfactants (e.g., Triton X100 and Laurylpropylamidobetaine) worked satisfactorily. We then inadvertently discovered that Laurylpropylamidobetaine and some other zwitterionic surfactants (e.g., DAPS and TDAPS) did not require protein buffering to delay red cell lysis, and are ideal alternate sphering agents for all kinds of blood cells for the methods of Kim and Ornstein. Because they do not require protein buffering, they permit a stable and simpler reagent to be manufactured. (The fixing steps of Kim and Ornstein are no longer obligatory; alternately, the problems of bacterial growth in protein-containing reagents is also avoided.) This invention is the subject of co-pending U.S. application Ser. No. 07/802,674, filed Dec. 5, 1991, now U.S. Pat. No. 5,284,771 entitled "Reagent Compositions and Their Use in Sphering Cells", filed concurrently herewith and assigned to the assignees of the present invention.

SUMMARY OF THE INVENTION

Accordingly, it is a principal object of the present invention to provide an improved reagent composition and method for differentiating reticulocytes from other cells in a blood sample by fluorescence flow cytometry.

Another object of the present invention is to provide reagent compositions and methods as above for enumerating reticulocytes in a whole blood sample by fluorescence flow cytometry.

A further object of the present invention is to provide a reagent composition and method as above for the simultaneous sphering of red blood cells and reticulocytes and staining of reticulocytes.

A yet further object of the present invention is to provide a reagent composition and method as above for simultaneously determining the volume, hemoglobin concentration and hemoglobin content of reticulocytes and erythrocytes in a whole blood sample by fluorescence and scattered light flow cytometry.

Still yet another object of the present invention is to provide a reagent composition and method as above for simultaneously discriminating between and counting each of the red blood cells and the reticulocytes within a blood sample, and determining the volume, hemoglobin content, hemoglobin concentration, mean erythrocyte volume, and mean corpuscular hemoglobin concentration of each cell type determined from measurements on a cell-by-cell basis.

Yet still another object of the present invention is to provide a reagent composition and method as above for simultaneously discriminating between and counting each of the red blood cells and the reticulocytes within a blood sample, and determining the volume, hemoglobin content, hemoglobin concentration, mean erythrocyte volume, and mean corpuscular hemoglobin concentration of each cell type determined from measurements on a cell-by-cell basis using a single red light laser source.

In accordance with one embodiment of the present invention, a reagent composition includes an organic cationic dye for staining the reticulocytes and a buffer solution for maintaining pH of about 6 to about 9. The dye may be the red excitable fluorescent dye Oxazine 750 having the structure:

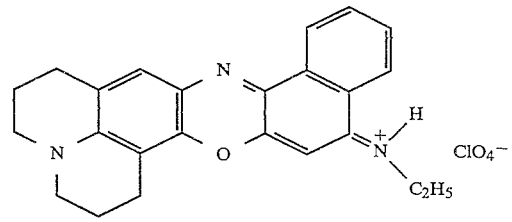

or blue excitable fluorescent dyes which are AO and quaternized derivatives of AO having the general structure:

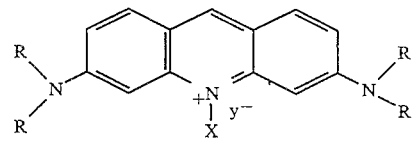

wherein: Y is an anion; R is independently a methyl or an ethyl group; and X is a hydroxyethyl group, or a benzyl group substituted in an ortho position with an $R_1$ group and/or in a para position with an $R_2$ group, wherein $R_1$ is a hydrogen atom or fluorine, and $R_2$ is a hydrogen atom, fluorine or a trifluoromethyl group.

Preferably, Y is an anion; R is a methyl group; and X is a hydroxymethyl group or a para substituted benzyl group. Most preferably, Y is bromide or iodide and X is a hydroxyethyl group.

The synthetic steps of producing quaternized derivatives of AO are described in the aforenoted U.S. patent application Ser. No. 07/444,255 to Fan, et al. Oxazine 750 is available from Exciton, Inc. of Dayton, Ohio. The preferred blue-excitable dye compounds of the present invention are 3,6-bis(dimethylamino)10-benzylacridinum bromide, 3,6-bis(dimethylamino)10-(2-fluoro)-benzylacridinum bromide, 3,6-bis(dimethylamino)10-(4-fluoro)-benzylacridinum bromide and 3,6-bis(dimethylamino)10-(4-trifluoromethyl)-benzylacridinium bromide and 3,6-bis(dimethylamino)-10-2-hydroxyethylacridinum iodide. The most preferred blue-excitable dye compound is 3,6-bis(dimethylamino)-10-2-hydroxyethyl acridinum iodide (AOEOH) because of the hydrophilic property of the hydroxyl group.

The reagent composition of the present invention includes the blue-dye compound present in an amount of from about 3 µg/ml to about 12 µg/ml (of a quaternized AO derivative for blue-excitable fluorescence staining), or from about 0.2 µg/ml to about 1.2 µg/ml of Oxazine 750 (for red-excitable fluorescence staining). Preferably, the dye compound is present in an amount of from about 6 µg/ml to about 9 µg/ml (of AOEOH), or from about 0.4 µg/ml to about 0.6 µg/ml (of Oxazine 750).

The buffer system of the reagent composition includes suitable buffers to maintain the pH of the reagent composition between about 6 and about 9. The solution may include one or more of the following constituents at the concentration noted, with the final osmolality adjusted with KCl or NaCl to from about 250 m Osm to about 330 m Osm:

| Constituent | Concentration (mM) |
| --- | --- |
| K/Na HCO$_3$ | 5-50 |
| Mg Cl$_2$ | 0-88 |
| KCl | 4-104 |
| Na$_3$PO$_4$ | 0-1.5 |
| CaCl$_2$ | 0-0.4 |

Preferably, the solution is formulated to maintain the pH of the reagent composition at between about 7 to about 8, and may include one or more of the following constituents in the concentration ranges given, and maintains an osmolality of about 280 m Osm to about 300 m Osm:

| Constituent | Concentration (mM) |
| --- | --- |
| Tris | 0-150 |
| K$_2$Ox | 0-121 |
| Barbital | 0-155 |

It has been found that the reagent composition should contain certain anions and cations to facilitate the dye penetration through the red cell membrane. Such anions may include bicarbonate, chloride, borate, barbital, oxalate (Ox) or ethylenediaminetetraacetic acid (EDTA). But not all anions have been found effective in promoting dye penetration across the cell membranes. For example, when one or more of the following anions: malate, tartarate, phosphate, were included in the reagent compositions as the only major anions, little, if any, distinction could be made between reticulocytes and erythrocytes. Possible cations include potassium, sodium, trishydroxymethylamino methane (Tris), or triethanolamine (TEA).

The reagent composition may be used to identify reticulocytes in a whole blood sample using the technique of scatter/fluorescence flow cytometry. The method in its broadest application includes mixing an aliquot of whole blood with one of the above reagent compositions. After a suitable incubation period, the sample/reagent mixture is then passed, one cell at a time, through a specific sensing region of the flow cytometer. By means of hydrodynamic focusing, single cells are passed through the sensing zone, where they are illuminated by a focused light source having a suitable illumination wavelength. At least one scattered light signal and at least one fluorescence signal are measured for the cells on a cell-by-cell basis. From these measurements, the reticulocytes can be distinguished from the erythrocytes.

In accordance with the preferred embodiment of the present invention, the above reagent composition further includes a zwitterionic surfactant to isovolumetrically sphere the red blood cells and reticulocytes. The zwitterionic sphering agent is preferably an alkyl amido betaine or an alkyl betaine such as lauramidopropyl-betaine (LAB).

To effectively isovolumetrically sphere the reticulocytes and red blood cells within a blood sample, the concentration of the sphering agent in the reagent composition is from about 12 µg/ml to about 87.5 µg/ml of LAB.

When this whole blood/reagent composition mixture is passed through the sensing region of a flow cytometer, the light scattered through two angular intervals and fluoresced by each cell is measured, the erythrocytes can be distinguished from reticulocytes and the volume and hemoglobin concentration of each reticulocyte or erythrocyte can be determined. The number of reticulocytes and erythrocytes, and the hemoglobin content, mean cell volume, mean corpuscular hemoglobin concentration, and mean cell hemoglobin of the reticulocytes or erythrocytes are calculated from the measured cell-by-cell volume and hemoglobin concentration. We have found that in the presence of the buffer systems described above, the concentration of Oxazine 750 or AOEOH in the reagent composition required for RNA staining is low, i.e., in the range of from about 0.2 µg/ml to about 1.2 µg/ml for Oxazine 750, and for AOEOH from about 3.0 to about 12 µg/ml, and the buffer enhanced penetration results in the dye staining RNA in the reticulocytes in less than 5 minutes. Such a low concentration of dye minimizes non-reticulocyte staining of mature erythrocytes and stream fluorescence which leads to a good signal separation from the noise background. Such rapid staining makes the reagent composition highly compatible with automated methods.

The invention accordingly comprises the compositions and methods hereinafter described, the scope of the invention being indicated in the claims.

BRIEF DESCRIPTION OF THE DRAWINGS

The above and other objects and significant advantages of the present invention are believed made clear by the following detailed description thereof taken in conjunction with the accompanying drawings wherein:

FIGS. 1A to 1E are schematic representations of the illumination optics, detection optics and detection signal processing systems, respectively, of scatter/fluorescence flow cytometers for practicing the principles of the present invention;

FIGS. 2A(1) and 2B(1) are cytograms of light scatter vs. fluorescence, and FIGS. 2A(2) and 2B(2) are cytograms of red light low angle scatter vs. red light high angle scatter for a whole blood sample containing reticulocytes stained with AOEOH and Oxazine 750, respectively, in accordance with Example 1.

FIGS. 6A and 6B are cytograms depicting the data obtained from Example 5.

DESCRIPTION OF THE PREFERRED EMBODIMENTS

Referring to FIGS. 1A through 1E, there are shown stylized, functional and structural representations of portions of flow cytometric apparatus which may be utilized in practicing the principles of the present invention. In fact, the apparatus depict particular systems which are modifications of a system commercially available under the trade designation TECHNICON H.1, sold by the assignee hereof.

The apparatus incorporate the principles of flow cytometry for cell analysis, and include the capacity for sensing the light scattering and fluorescent responses of cells to specific types of illumination. Only those components of primary interest with respect to the invention are shown. Thus, the drawings do not illustrate all of the mechanical and electrical elements, i.e., motors, solenoids, pumps, valves, sensors, required for driving and controlling the various components of the apparatus. All of these elements may have any known, conventional form, which can readily be realized by one of normal skill in the art having knowledge of the information hereinafter given with regard to the desired mode of operation of the various components in a flow cytometric apparatus according to the invention for treating the samples in the manner intended.

Described in its most general terms, a sheath-stream flowcell and supporting hydraulics deliver prepared cells to the point of measurement. The cells are confined to a cylindrical volume which is central to the square-cross-section flow channel of the flowcell. The flowcell construction is identical to that used in the TECHNICON H.1 system with one exception. The flow cell body is made of synthetic fused silica (rather than glass) to minimize background fluorescence from the flowcell itself. The hydraulic system is quite simple, consisting of only two peristaltic pumps and their associated tubing. The sheath pump and tube deliver the sheath at a rate of $1.6 \times 10^{-7}$ m³/sec; the sample is delivered at a rate of $3.5 \times 10^{-10}$ m³/sec; the flow channel within the flowcell is 250 μm by 250 μm. The resulting cylindrical sample stream has a diameter of 7 μm and a velocity of 2.5 m/s.

The primary objective is to provide an optical system which will, at a minimum, support a single color fluorescence measurement, in addition to the two red cell scatter channels required by the TECHNICON H.1 system for red cell analysis. As will be discussed, the optical system used will depend upon the particular dye, i.e., blue excitable or red excitable, used to stain the cells. The optical system of the scatter/fluorescence flow cytometer can be divided generally into two subsystems: a) the illumination optics (FIG. 1A or 1D); and b) the collection optics (FIG. 1B or 1E).

Figure 1A:
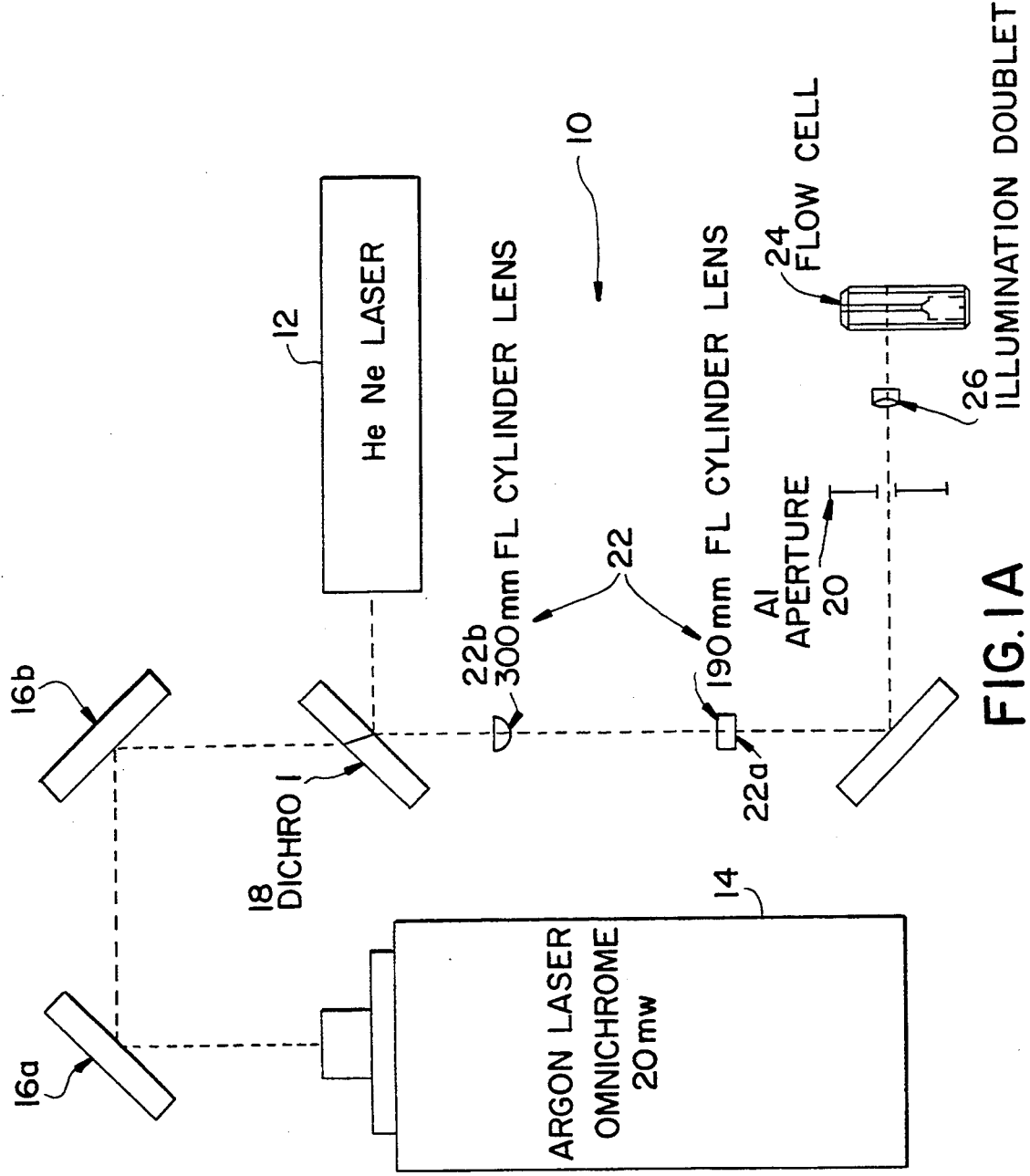
Figure 1B:
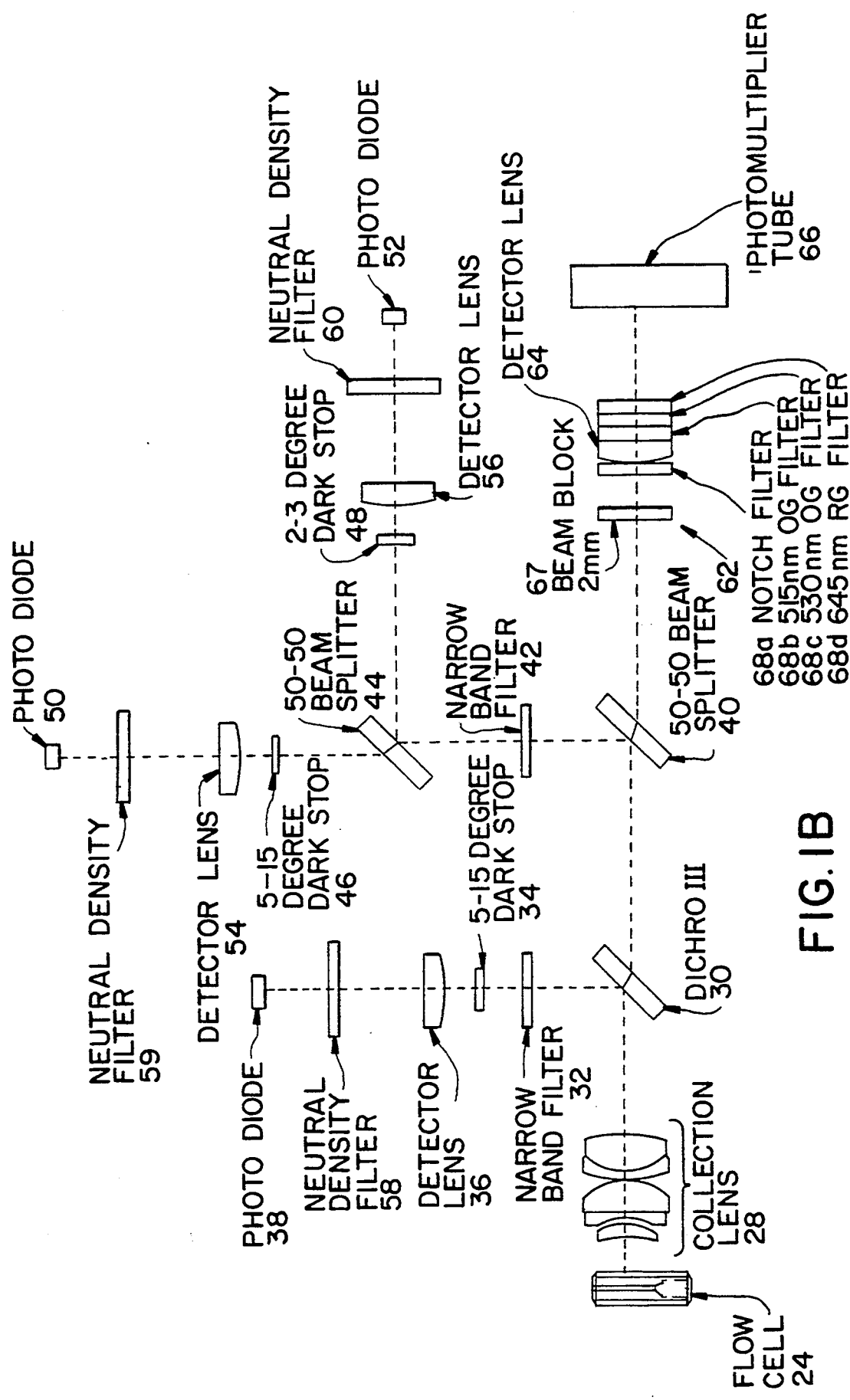

Referring first to FIG. 1A, the illumination optics for a blue excitable dye is generally identified by the reference numeral 10, and incorporates two light sources. A helium-neon (HeNe) laser 12 emits light at 633 nM and 2 mW, required for red cell scatter measurements for determination of volume and hemoglobin concentration. An argon ion laser 14, which emits light at 488 nm and 20 mW, is required for fluorophore excitation. Three relay mirrors 16a, 16b and 16c, and a dichroic beamsplitter 18 are needed for proper alignment of the illumination system. The beams from the lasers are made collinear at beamsplitter 18, which transmits the blue light from the argon ion laser 14, and reflects the red light from the HeNe laser 12. The resulting beam is then shaped into an ellipse at a rectangular aperture (A-1) 20 by a pair of crossed cylinder lenses 22. The focal length of the cylinder lens 22a closest to the A-1 aperture is 150 mm. The central axis of this lens is parallel to the long dimension of the aperture. The second cylinder lens 22b has a focal length of 300 mm. The rectangular aperture, which is 89 μm high by 653 μm wide, is imaged into the flow cell 24 using a diffraction-limited achromatic lens 26 to define the measuring volume. The overall magnification is approximately 0.25. The aperture is underfilled in the long dimension and overfilled in the short dimension. The objectives here were to maximize the illumination intensity and maintain a flat intensity distribution in the short dimension of the image in order to minimize errors due to intensity variation from cell to cell. The measuring volume is essentially elliptical in shape and is 20 μm high by 65 μm wide at the $1/e^2$ points. The minor axis of the ellipse is parallel to the direction of flow which is vertical with respect to the horizon.

Cells which pass through the measuring volume scatter incident radiation. Stained cells also absorb incident radiation. The stained cells also fluoresce, emitting energy at a frequency lower than that which was absorbed. These optical signals are captured and detected in the capture optics illustrated in FIG. 1B.

The light scattered and fluoresced by cells traversing the measuring volume is collimated by collection lens 28, and then separated into four channels. The numerical aperture of the collection lens is 0.34. At beamsplitter 30, light with a wavelength below 500 nm is reflected. This light is filtered again using a 488 nm narrow band interference filter 32. An annular dark field stop 34 is used to transmit only blue light scattered into the angular interval from 5-15 degrees. The scattered light is then focused by detector lens 36 onto a silicon photodiode 38 where electronic signals are generated.

The remaining light is equally split into two beams at beamsplitter 40. Half of the energy is reflected to the red scatter channels and half is transmitted to the red fluorescence channel. (This beamsplitter 40 may be replaced with the appropriate dichroic beamsplitter to improve the signal-to-noise ratio in the fluorescence channel.) The light reflected towards the red scatter channels is filtered using a 633 nm narrow band interference filter 42, and then split by the 50/50 (50% reflection, 50% transmission) beamsplitter 44 into two beams. Dark stops 46 and 48 are used in these two red scatter channels to collect light in the two angular intervals required to determine cell V and HC. The scattered light in each channel is focused onto each of two silicon photodiodes 50 and 52 by detector lenses 54 and 56, respectively, where electrical signals are generated. Neutral density filters 58, 59 and 60 are used in each scatter channel, blue and red, to adjust the dynamic range of signals simply without modifying the preamplifier circuit.

The light transmitted by beamsplitter 40 is filtered at 62 to allow only fluorescent energy to pass, and then focused by detector lens 64 onto a photomultiplier tube 66, through a 1 mm diameter pinhole, where electrical signals proportional to the magnitude of the incident energy are generated. The presence of the pinhole minimizes shot noise produced by extraneous light. A 2 mm wide blocking bar 67 positioned before the detection lens intercepts the main beam further reducing background light noise. There is a sandwich of four filters 68 in this channel, comprising a 633 Notch Filter (X2) 68a, a Schott OG515 Color Glass 68b, a Schott OG530 Color Glass 68, and a Schott RG645 Color Glass 68d.

The net effect of this filter combination will be the blockage of all light below 645 nm. The notch and OG filters 68a, 68b and 68c are required since the RG645 filter 68d is not efficient enough to block completely the scattered light at 633 nm and 488 nm.

The gain of the preamplifier circuit and optical density of the neutral density filter in each scatter channel were chosen to produce mean pulse signal levels of approximately 2 volts at the output of each channel when Technicon (TCN) optical test material (OTM TCH T03-1704) was assayed. OTM consists of sphered and hard-fixed red blood cells. This material is commercially available from the assignee hereof, and is adapted for use on the TECHNICON H.1 system. This then allows fine adjustment of the overall gain in each channel using a variable gain amplifier in the post-signal-detection-processing-hardware. The overall gain in the fluorescence channel is controlled by adjustment of the high voltage feeding the photomultiplier tube.

A functional block diagram of the post-detection signal processing system is shown in FIG. 1C. This system includes preamplifiers 67, a variable gain amplifier 68, pulse height analyzer 70, analog-to-digital converter 72, and data acquisition hardware (computer) 74 and software.

The variable gain amplifier 68 contains four circuits which permit inversion and amplitude conditioning of up to four input signals.

The pulse-height analyzer 70, analog-to-digital converter 72 and data acquisition software are all components of the 4Cyte system which was purchased from Howard Shapiro, M.D., P.C. of Cambridge, Mass. The pulse-height analyzer is the 4Cyte Model FE Front End. This component produces held pulses, representing the pulse heights, for up to four input signals, and allows setting of the "valid" pulse height threshold level. The 4Cyte Model I interface card is used in conjunction with the 4Cyte software for analog-to-digital conversion of up to four input signals, and the capture of those values in the RAM memory of the host computer. The digitized signals are stored in list mode.

There are five eight-bit bytes of information for each cell, one for each of the four parameters measured and one for flagging. The host computer for these experiments was an IBM PC/XT clone equipped with a color monitor and a math co-processor. Data reduction can be performed on any IBM compatible computer.

Figure 1D:
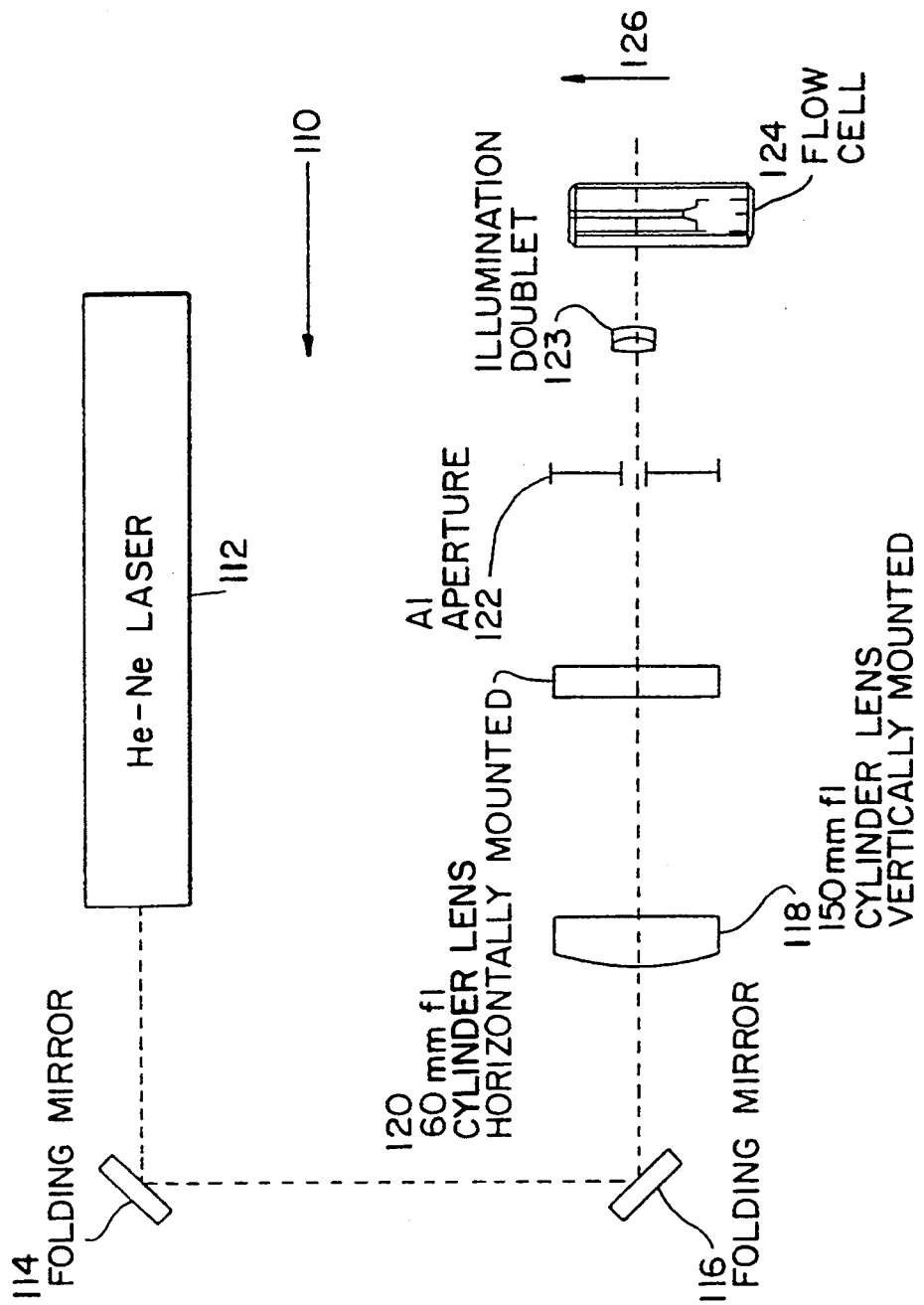
Figure 1E:
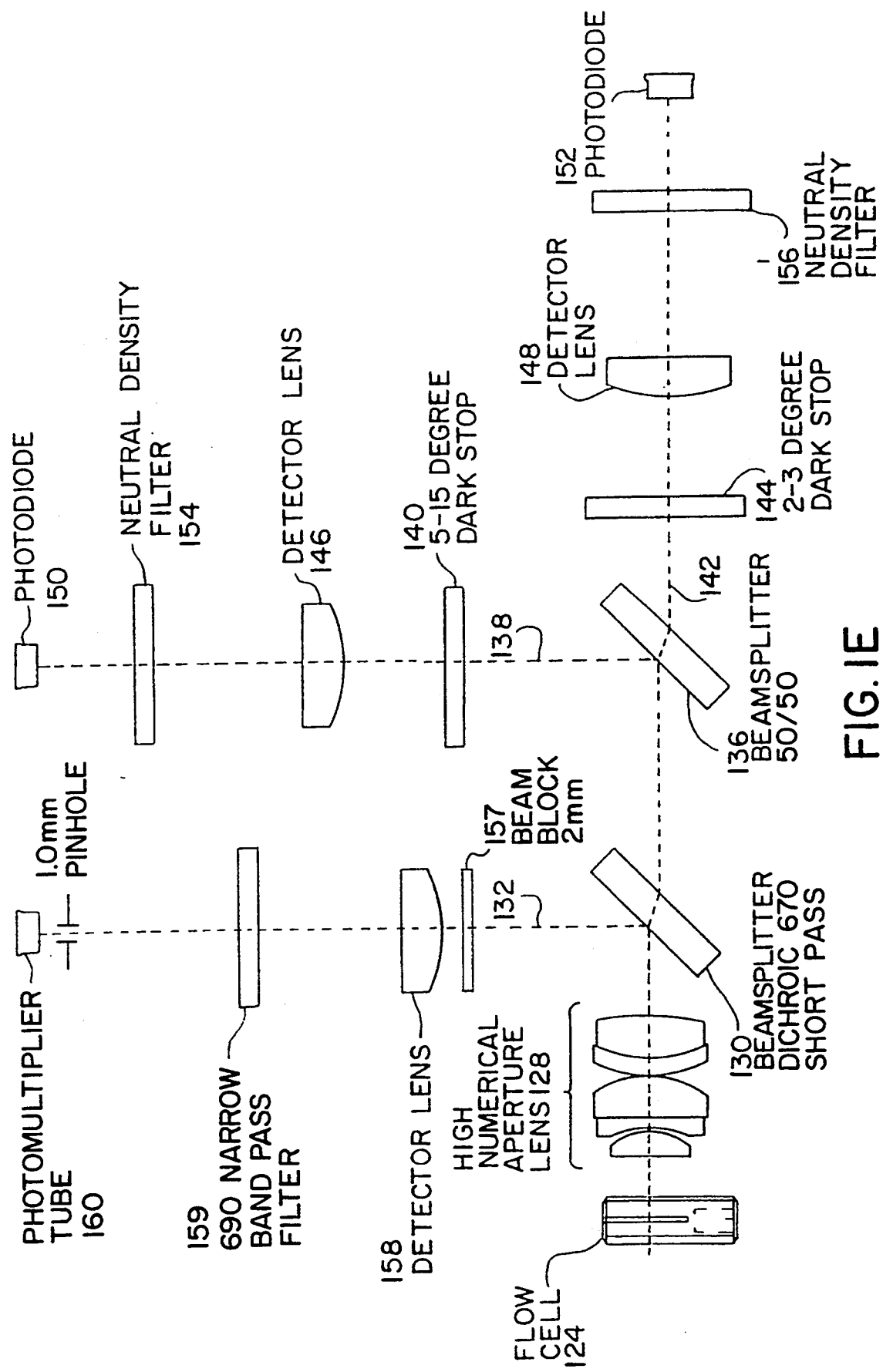

Turning now to FIG. 1D, the illumination optical system for a red excitable dye is generally identified by the reference numeral 110, and incorporates a helium-neon laser 112 that emits a 2 mW beam of light at 633 nm. The beam is folded by two reflecting mirrors 114 and 116 that provide adjustment of the laser beam position. The adjustment enables the beam axis to coincide with the physical optical axis of the illumination optics. The beam is then shaped by the pair of cyliner lenses 118 and 120 into a 192×77 µm elliptically shaped beam (at the $1/e^2$). The 192 µm dimension is formed by the 150 nm focal length cylinder lens 118, and it illuminates the long axis of the A-1 aperture 122 (which is parallel to the plane of the page in FIG. 1D). The 77 µm dimension is formed by the 60 mm focal length cylinder lens 120, and it illuminates the short axis of the A-1 aperture. The A-1 aperture is 653 ×89 µm. The illumination doublet 123 produces an elliptically shaped Gaussian intensity distribution of 37.4 ×12.6 µm in the flowcell 124. The minor axis of the ellipse is parallel to the direction of flow, which is vertical, i.e., in the direction of arrow 126.

All cells that pass through the measuring volume scatter and absorb the incident radiation. The light scattered and fluoresced is captured and measured in the detection optics illustrated schematically in FIG. 1E. The light that is scattered and fluoresced is collected by the high numerical aperture (Hi-NA) lens 128 and collimated. The numerical aperture of the collection lens is 0.34 nm. The beam is divided into two parts by the dichroic beamsplitter 130, which allows light at wavelengths less than 670 nm to pass. The beam 132 is reflected onto a photomultiplier after filtering, and is used for the fluorescence measurement, while the transmitted beam 134 is further split by the 50/50 (50% reflection, 50% transmission) beamsplitter 136 to make the two scatter channels. The reflected scatter channel 138 has a 5°-15° darkstop 140, while the transmitted channel 142 has a 2°-3° darkstop 144. The light passing through each of these darkstops 140, 144 is then focused down through lenses 146 and 148 onto photodiodes 150 and 152, respectively. Neutral density filters 154 and 156 are used to reduce the light levels at each photodiode to a level that is appropriate for the standard detectors and preamplifiers.

The light reflected by the beamsplitter 130 is focused by lens 158 through a narrow band (690 nm) filter 159, through a 1 mm diameter pinhole onto a photomultiplier tube 160, where electrical signals, proportional to the magnitude of the incident energy are generated. A 2 mm wide blocking bar 157 positioned before the detection lens 158 intercepts the main beam further reducing background light noise. The signals generated by the photodiodes 150, 152 and the photomultiplier tube 160 are processed in a post-detection signal processing system similar to that shown in FIG. 1C. In this case, however, only three signals, i.e., red low angle scatter, red high angle scatter and red fluorescence, are processed (not the four signals discussed with respect to FIG. 1C).

The following examples set forth reagent compositions and methods incorporating the same for the identification of reticulocytes and characterization of reticulocytes and red blood cells using fluorescence flow cytometry techniques. Standard commercially available reagent grade materials were used whenever possible. It will be understood that the formulations and the procedures which follow are provided for purpose of illustration only, and that other ingredients, proportions and procedures can be employed in accordance with the disclosures of this invention.

EXAMPLE 1

Scatter and Fluorescence Measurements for Distinguishing Reticulocytes and Erythrocytes Within a Blood Sample Using Reagent Composition Containing a Zwitterionic Surfactant The dye 3,6-bis(dimethylamino)-10-2-hydroxyethyl acridinum iodide (AOEOH) was stored in a 1 mg N,N-dimethylformamide/ml stock solution. A working reagent was created by adding the dye stock to give a final concentration of 6 $\mu$g/ml to 12 $\mu$g/ml of dye. The final concentration of lauramidopropyl betaine was from 12 $\mu$g/ml to 87.5 $\mu$g/ml. A buffer solution contained the following components at the concentrations noted:

| | |
|---|---|
| Calcium Chloride | 0.4 mM |
| Potassium Chloride | 4.0 mM |
| Magnesium Chloride | 40.0 mM |
| Sodium Phosphate (Tribasic) | 0.5 mM |
| Sodium Bicarbonate | 20.0 mM |

The final osmolality and pH of the working reagent used in this study were 272 mmol/kg and 8.1, respectively.

Samples were hand-mixed in a manner which simulated the automated TECHNICON H.1 red cell sample processing scheme. Glass test tubes were filled with 5 milliliters of the working reagent. Five microliters of a blood sample were then pipetted into the reagent while the reagent was undergoing agitation on a vortex mixer. The 1:1000 dilution of blood was then fed immediately into the sample line of the previously described flow cytometric apparatus and the optical system of FIGS. 1A and 1B. In approximately two minutes, the sample passed through the flow cell and was exposed to an argon-ion laser source for red cell and reticulocyte analysis. Each sample was measured in duplicate if the sample volume permitted.

When viewed through a microscope, the mature red cells and reticulocytes in a prepared sample were found to be sphered, and the reticulocytes fluoresced in the red when excited by blue light.

At the completion of the analysis, the raw data was displayed in the form of a Blue Scatter v. Red Fluorescence cytogram, FIG. 2A(1), wherein the ordinate represents the relative intensity of forward scattered light, and the abscissa represents the relative intensity of red fluorescence. Each point shown on the cytogram represents a cell. Distinct cell populations were clearly observed based on their particular scatter and fluorescence signals. The mature erythrocyte population falls within Region A between the ordinate and the vertical line X. These cells show high scatter signals and low cell fluorescence signals. The reticulocyte population falls within the region to the right of X, Region B. These cells are distinguishable from the mature erythrocytes due to the high fluorescence signals from their AOEOH stained RNA. The platelet population lies within Region C below line Y. Platelets have relatively low scatter signals when compared to the reticulocytes.

Based on the fluorescence separation between mature erythrocytes and reticulocytes, the reticulocyte count of a patient sample may be determined by creating an electronic "window" which defines the ranges of scattered light and fluorescence which identify reticulocytes and mature erythrocytes. The number of reticulocytes and mature erythrocytes falling within the "window" are determined so that the percentage of the reticulocytes and erythrocytes present in the total cell population is known. In FIG. 2A(1), the reticulocyte "window" is determined by Region B, and the mature erythrocyte "window" by Region A. Note in FIG. 2A(2) and in all following scatter/scatter cytograms, the non-linear grid overlays indicate the loci of constant volume and constant refractive index for perfect spheres according to the above-noted method of Tycko.

The reference percentage of reticulocytes in each sample was determined using the manual microscopic procedure recommended by the National Committee for Clinical Laboratory Standards (NCCLS). In this procedure, a small volume of the sample was vitally stained with New Methylene Blue. A conventional dry wedge smear was then prepared, and the percentage of reticulocytes in the sample was counted with the aid of a microscope. The microscope was equipped with a 100X oil immersion objective and a 10X ocular. A minimum of 1000 cells were counted for each sample. A Miller disc was inserted in the ocular of the microscope to improve counting precision. Any red cell containing two or more particles of blue material after staining was labeled a reticulocyte.

The reticulocyte count of the patient sample was measured to be 1.7% by this flow cytometric technique. The same blood sample was also analyzed by the NCCLS method. The result was a reticulocyte count of 1.7%.

A second experiment was conducted to demonstrate the high degree of discrimination between reticulocyte and erythrocyte populations when cells were stained with Oxazine 750 and measured by the previously described fluorescence flow cytometer and optical system of FIGS. 1D and 1E. Oxazine 750 dye was stored in a 1 mg N,N-dimethylformamide/ml stock solution. A working reagent was created by adding the dye stock to a final concentration of from 0.2 $\mu$g/ml to 1.2 $\mu$g/ml, to the sphering agent and the buffer solution described above.

Figure 2C:
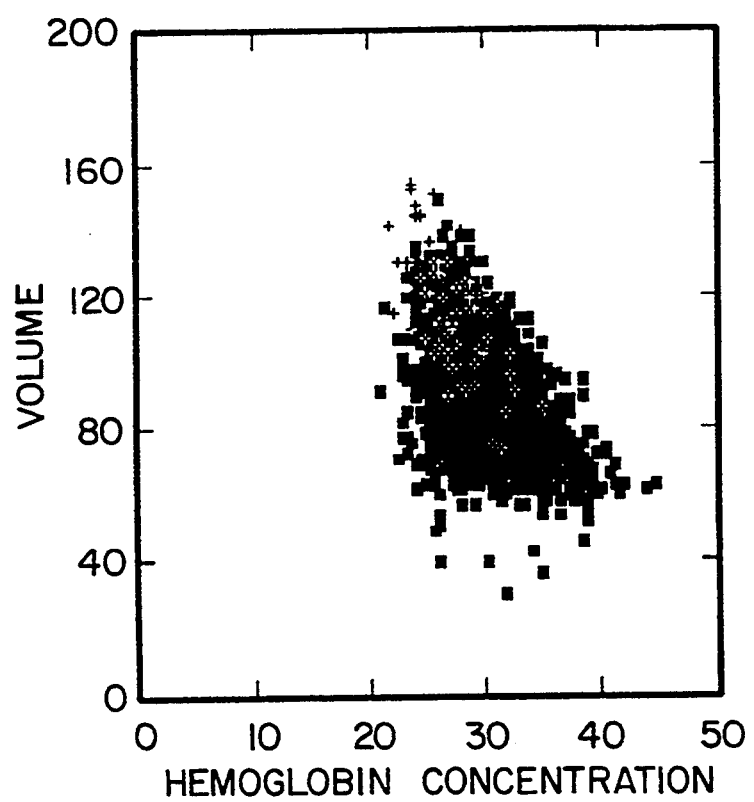
FIG. 2C is a cytogram of HC vs. V with reticulocytes identified by "+" and red cells by "▩"

The sample preparation protocols as described above were followed. FIG. 2B(1) displays the fluorescence vs. low angle scatter cytogram of a normal human blood sample stained with the Oxazine 750 containing reagent. Based on the fluorescence separation between erythrocytes and reticulocytes, the reticulocyte count of the sample was measured as 2.1%. When analyzed by the NCCLS method, a reticulocyte count of 2.1% was obtained. FIG. 2C shows the reticulocyte as "+" superimposed on mature erythrocytes obtained from similar data as FIGS. 2A and 2B.

EXAMPLE 2

Correlation Study with the Reagent Compositions and Methods of the Present Invention and the NCCLS Method A study was conducted to compare the performance of AOEOH when used in a reagent composition in the previously described fluorescence flow cytometer and the optical system of FIGS. 1A and 1B and the NCCLS manual method. Blood samples were obtained from 39 Technicon employees and 23 hospital patients. The hospital samples included three sickle cell, one thalassemia and ten neo-natal blood samples. The 62 blood samples were stained with the reagent composition described in Example 1, and assayed for their reticulocyte content. Reticulocytes in the same set of blood samples were also counted using the NCCLS method.

The sample preparation and analysis protocols as described above with regard to Example 1 were followed.

Figure 3B:
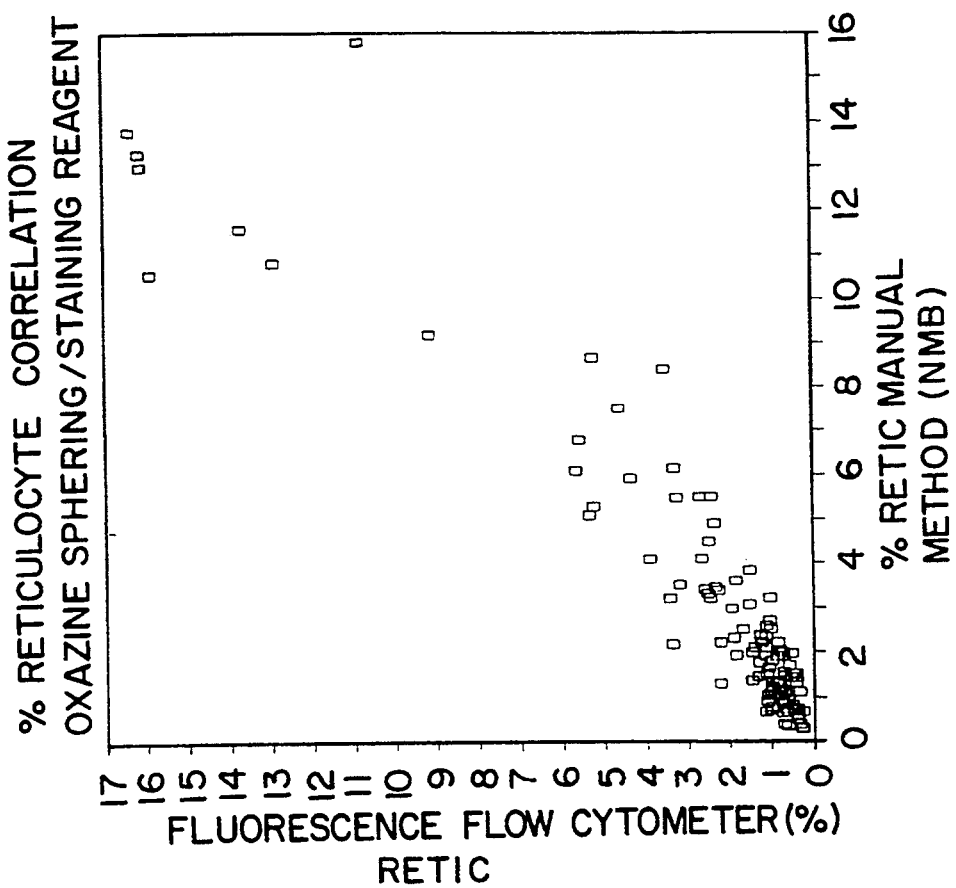
FIGS. 3A and 3B show the comparison of the percentage of reticulocytes detected in a whole blood sample using the AOEOH and Oxazine 750 reagents, respectively, and the NCCLS reference method in accordance with Example 2.
Figure 3A:
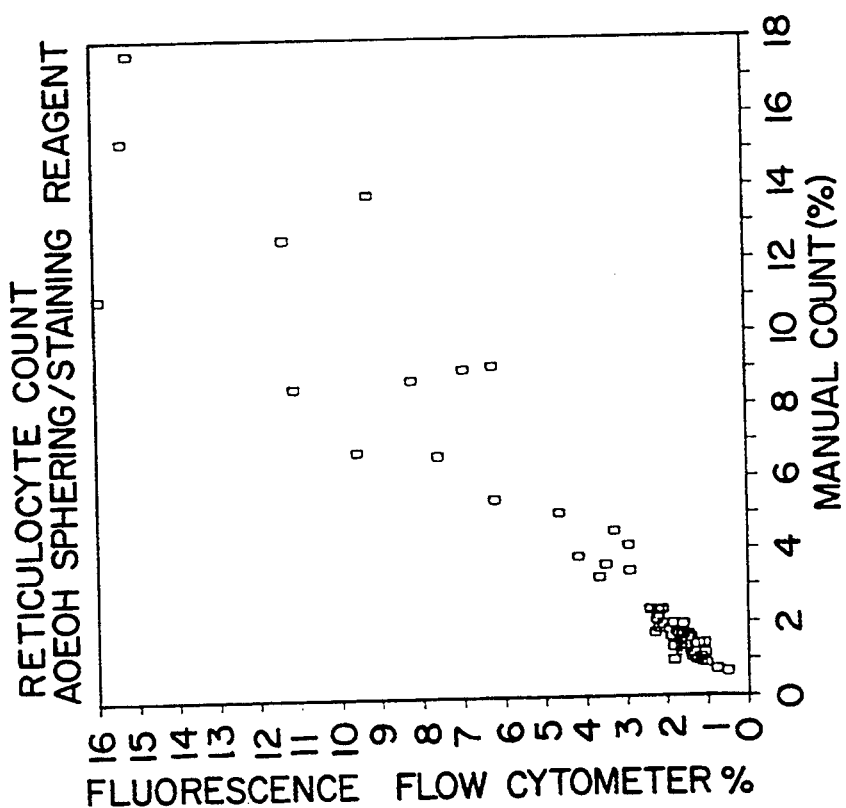

The percentage reticulocyte counts obtained from these two methods are compared in FIG. 3A. At a concentration of 6 ug AOEOH/ml in the reagent composition, close correlation was shown to exist between the reagent composition and measurements obtained using the previously described fluorescence flow cytometer and the optical system of FIGS. 1A and 1B and those obtained by the NCCLS reference method. The correlation coefficient for the measurement was 0.95.

A second experiment was conducted to compare the performance of Oxazine 750 reagent when used in the previously described fluorescence flow cytometer and the optical system of FIGS. 1D and 1E and the NCCLS method. The sample preparation and analysis protocols of Example 1 were followed. Blood samples were stained with the reagent composition and assayed for their reticulocyte content. Reticulocytes in the same set of blood samples were also counted using the NCCLS method. The percentage reticulocyte counts obtained from these two methods are compared in FIG. 3B. The correlation coefficient for the measurement was 0.93.

EXAMPLE 3

Correlation Study with the AOEOH Containing Reagent Composition of the Present Invention and the TECHNICON H.1 Jr. Reference Method The same set of samples in Example 2 were also measured using the TECHNICON H.1 Jr. system for the red cell indices. The TECHNICON H.1 Jr. automated system is a flow cytometer that simultaneously measures the cell volume and hemoglobin concentration of individual isovolumetrically sphered red blood cells.

Figure 4B:
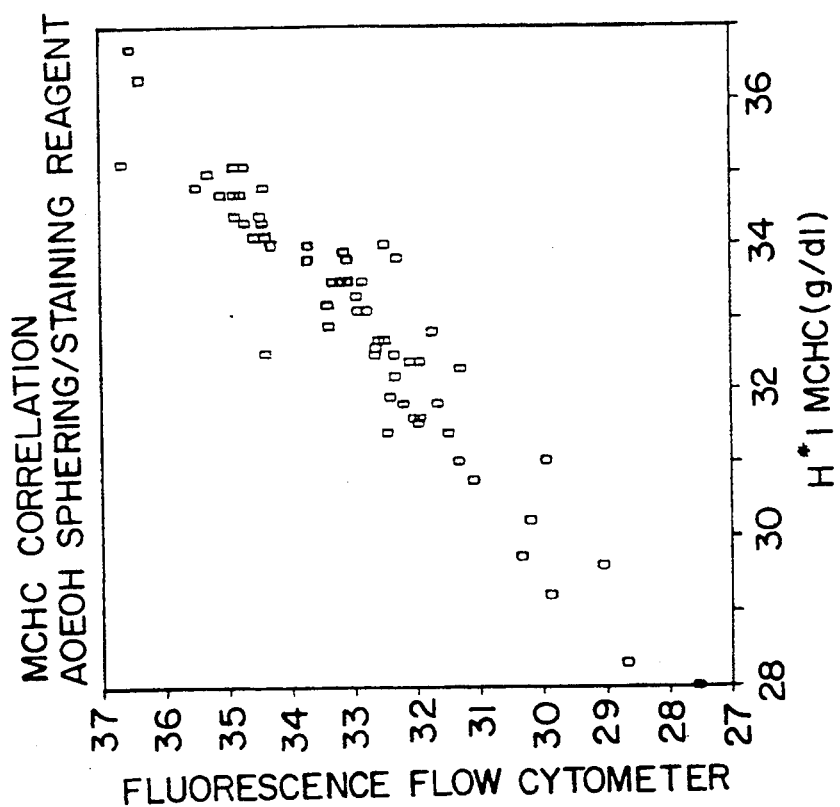
FIGS. 4A and 4B show the correlation between the MCV and MCHC data for reticulocytes stained with the AOEOH containing reagent and the TECHNICON H.1 Jr. reference method, in accordance with Example 3.
Figure 4A:
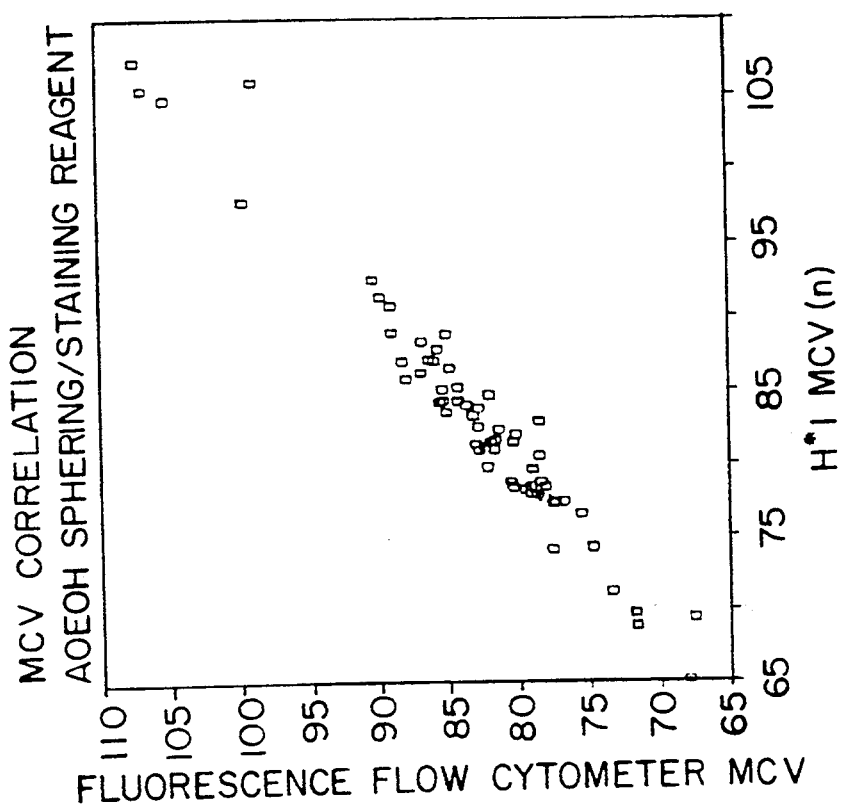

The indices, MCV and MCHC were separately determined on the TECHNICON H.1 Jr. analyzer, and compared with the values obtained using the AOEOH containing reagent composition of the present invention. FIGS. 4A and 4B show the correlation data for total red blood cell indices, MCV and MCHC, respectively. The correlation coefficients for the measurement were 0.91 and 0.97, respectively.

EXAMPLE 4

Figure 5B:
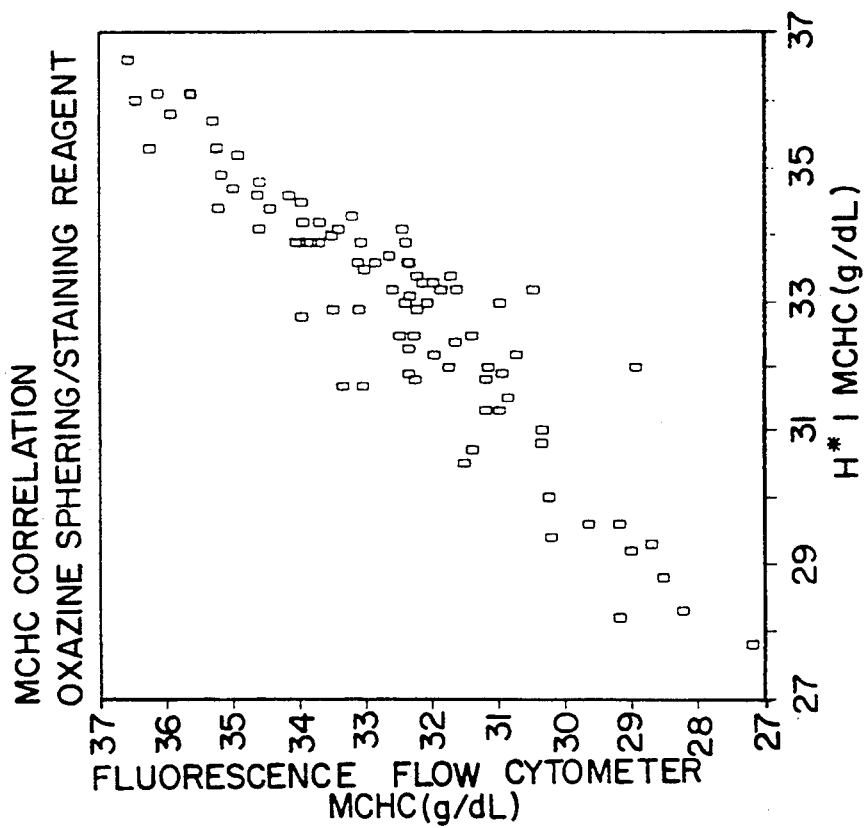
FIGS. 5A and 5B show the correlation between the MCV and MCHC data for reticulocytes stained with Oxazine 750 containing reagent and the TECHNICON H.1 Jr. reference method in accordance with Example 4.
Figure 5A:
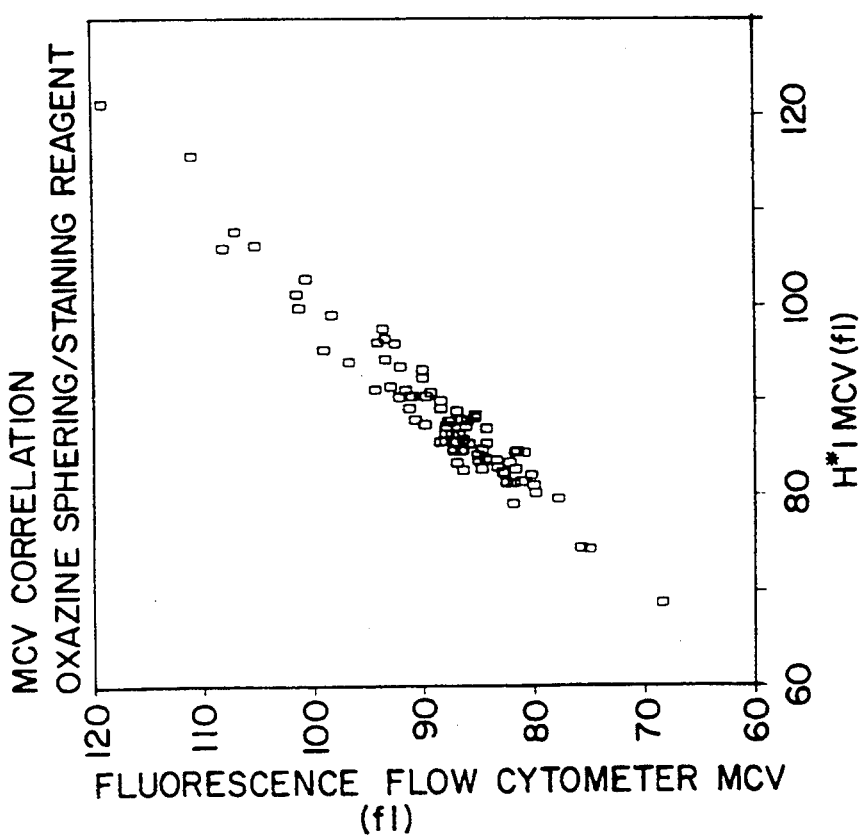

Correlation Study with the Oxazine 750 Containing Reagent Composition of the Present Invention and the TECHNICON H.1 Reference Method The erythrocyte and reticulocyte indices, MCV and MCHC were separately determined and compared with the values obtained using the Oxazine 750 reagent composition of the present invention. FIGS. 5A and 5B show the correlation data for total red blood cell MCV and MCHC, respectively.

The correlation coefficients for the measurement were 0.93 and 0.92, respectively.

EXAMPLE 5

Scatter and Fluorescence Measurements for Distinguishing Reticulocytes and Erythrocytes Within a Blood Sample Using the Reagent Composition of Example 2 Containing AOEOH and a Buffer, Which Fails to Distinguish Reticulocytes Within Blood Not all buffers can be used to stain and sphere reticulocytes simultaneously. This example demonstrates a poor discrimination between reticulocytes and erythrocytes when using AOEOH staining dye and phosphate buffer at pH 8.0 and osmolality of 290 m Osm (see FIG. 6A). In comparison, a good separation between reticulocytes and erythrocytes is clearly observed when using Barbital buffer (12 ug/ml LAB surfactant) at pH 8.0 and osmolality 290 m Osm (see FIG. 6B).

Some advantages of the present invention evident from the foregoing description include a reagent composition and method for the identification of reticulocytes in a whole blood sample, and for the simultaneous quantitation of the volume, hemoglobin content and hemoglobin concentration of reticulocytes and erythrocytes by fluorescence flow cytometric techniques.

In view of the above, it will be seen that the several objects of the invention are achieved, and other advantageous results obtained.

As various changes can be made in the above constructions and methods without departing from the scope of the invention, it is intended that all matter contained in the above description, or shown on the accompanying drawings, shall be interpreted as illustrative, not in a limiting sense. For instance, fractionated samples of blood can be processed in a similar way.

What is claimed is:

1. A reagent composition for the characterization by flow cytometry of reticulocytes in a whole blood sample comprising reticulocytes and erythrocytes, said reagent composition comprising an effective amount of a red-excitable fluorescent, organic cationic dye compound for staining ribonucleic acid within said reticulocytes, an amount of a zwitterionic surfactant sufficient to effect isovolumetric sphering of said reticulocytes and erythrocytes without precipitating said dye; and a buffer solution for maintaining the pH of said composition at about 6 to about 9.

2. The reagent composition according to claim 1, wherein said dye compound is Oxazine 750 having the formula:

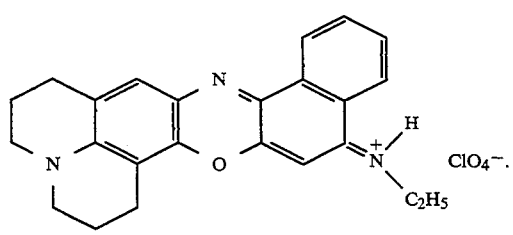

3. The reagent composition according to claims 1 or 2, wherein said buffer solution comprises one or more of: K/NaHCO$_3$ at a concentration of from about 5 mM to about 50 mM; Mg Cl$_2$ at a concentration of from about 0 mM to about 88 mM; KCl at a concentration of from about 4 mM to about 104 mM; Na$_3$PO$_4$ at a concentration of from about 0 mM to about 1.5 mM; and CaCl$_2$ at a concentration of from about 0 mM to about 0.4 mM; such that the final osmolality of the reagent composition is from about 270 m Osm to about 310 m Osm.

4. The reagent composition according to claims 1 or 2, wherein said buffer solution comprises one or more of: Tris at a concentration of from about 0 mM to about 150 mM; K$_2$Ox/EDTA at a concentration of from about 0 mM to about 121 mM; and Barbital at a concentration of from about 0 mM to about 155 mM; such that the final osmolality of the reagent composition is from about 280 m Osm to about 300 m Osm.

5. The reagent composition according to claim 4, wherein the pH of said composition is about 7 to about 8.

6. The reagent composition according to claims 1 or 2, wherein said dye compound is present at a concentration of from about 0.2 µg/mL to about 1.2 µg/mL.

7. The reagent composition according to claim 3, wherein said Oxazine 750 is present at a concentration of from about 0.4 µg/mL to about 0.6 µg/mL.

8. The reagent composition according to claims 1 or 2, wherein said zwitterionic surfactant is present at a concentration of from about 12 µg per ml to about 87.5 µg per ml.

9. The reagent composition according to claims 1 or 2; wherein said surfactant is an alkylamidobetaine or an alkyl betaine.

10. The reagent composition according to claim 9, wherein said surfactant is lauramidopropylbetaine.

11. The reagent composition according to claim 1 or 2, wherein said composition further comprises one or more anions selected from the group consisting of bicarbonate, chloride, borate, barbital, oxylate, and ethylenediaminetetraacidic acid, or one or more cations selected from the group consisting of potassium, sodium, trishydroxymethylamino methane, and triethanolamine, or mixtures thereof.

* * * * *

UNITED STATES PATENT AND TRADEMARK OFFICE
CERTIFICATE OF CORRECTION

PATENT NO. : 5,411,891
DATED : May 2, 1995
INVENTOR(S) : Sophie S. FAN et al.

It is certified that error appears in the above-indentified patent and that said Letters Patent is hereby corrected as shown below:

Column 20, Claim 7, line 1, please delete "claim 3" and insert -- claim 2 --.

Signed and Sealed this

Nineteenth Day of September, 1995

Attest:

BRUCE LEHMAN

*Attesting Officer*   *Commissioner of Patents and Trademarks*